(12) United States Patent
Tamez-Pena

(10) Patent No.: US 11,210,790 B1
(45) Date of Patent: Dec. 28, 2021

(54) SYSTEM AND METHOD FOR OUTCOME-SPECIFIC IMAGE ENHANCEMENT

(71) Applicant: 4QIMAGING, LLC, Pittsford, NY (US)

(72) Inventor: Jose G. Tamez-Pena, San Pedro Garza Garcia (MX)

(73) Assignee: 4QIMAGING, LLC, Pittsford, NY (US)

(*) Notice: Subject to any disclaimer, the term of this patent is extended or adjusted under 35 U.S.C. 154(b) by 154 days.

(21) Appl. No.: 16/810,393

(22) Filed: Mar. 5, 2020

Related U.S. Application Data

(60) Provisional application No. 62/813,950, filed on Mar. 5, 2019.

(51) Int. Cl.
*G06T 7/00* (2017.01)
*G06T 7/11* (2017.01)
(Continued)

(52) U.S. Cl.
CPC .......... *G06T 7/0014* (2013.01); *A61B 5/0042* (2013.01); *A61B 5/055* (2013.01); *A61B 5/4064* (2013.01); *A61B 6/037* (2013.01); *A61B 6/501* (2013.01); *G06T 7/11* (2017.01); *G06T 7/73* (2017.01); *G06T 2207/30016* (2013.01)

(58) Field of Classification Search
CPC ..... A61B 5/0042; A61B 5/055; A61B 5/4064; A61B 6/037; A61B 6/501; G06T 7/11; G06T 7/73; G06T 2207/30016
See application file for complete search history.

(56) References Cited

U.S. PATENT DOCUMENTS

2004/0127799 A1\* 7/2004 Sorensen .............. G06T 7/0012 600/481
2007/0167727 A1\* 7/2007 Menezes .............. G06T 7/0012 600/410
(Continued)

OTHER PUBLICATIONS

Tamez-Pena, Jose G.; "Feature Selection and the BSWiMs Method"; ResearchGate; Tecnologico de Monterrey; Nov. 2018; uploaded on Dec. 4, 2018.

*Primary Examiner* — Katrina R Fujita
(74) *Attorney, Agent, or Firm* — Woods Oviatt Gilman LLP; Dennis B. Danelia, Esq.

(57) ABSTRACT

A system and method for predicting an outcome specific signal (OSS) in test subject images. The method includes detecting the OSS in image data from outcome and control subjects; extracting a volumetric space containing the detected OSS and dividing the extracted volumetric space into a first set of sub-regions; determining a set of image features for the first set of sub-regions; determining a global feature set (GFS) by averaging the set of image features; utilizing a machine learning algorithm to select a subset of discriminant GFS to determine a best signal model (BSM) that distinguishes the outcome and control subjects; extracting volumetric space containing the target anatomy in test subject images and dividing the extracted volumetric space into a second set of sub-regions; and determining the subset of discriminant GFS at each of the second set of sub-regions, and using them in the BSM to generate the predicted OSS.

18 Claims, 9 Drawing Sheets
(7 of 9 Drawing Sheet(s) Filed in Color)

(51) Int. Cl.
*G06T 7/73* (2017.01)
*A61B 5/00* (2006.01)
*A61B 6/03* (2006.01)
*A61B 6/00* (2006.01)
*A61B 5/055* (2006.01)

(56) References Cited

U.S. PATENT DOCUMENTS

| | | | | |
|---|---|---|---|---|
| 2009/0024181 A1* | 1/2009 | Raghavan | A61B 6/501 | 607/45 |
| 2013/0303900 A1* | 11/2013 | Nowinski | A61B 6/501 | 600/425 |
| 2013/0329973 A1* | 12/2013 | Cao | G06T 7/0016 | 382/128 |
| 2015/0379713 A1* | 12/2015 | Puybasset | G16H 30/40 | 382/131 |
| 2016/0045128 A1* | 2/2016 | Sitt | A61B 5/291 | 600/409 |
| 2016/0067007 A1* | 3/2016 | Piron | G16H 50/70 | 705/3 |
| 2016/0378919 A1* | 12/2016 | McNutt | G16H 20/40 | 705/3 |
| 2017/0046839 A1* | 2/2017 | Paik | G06K 9/00147 | |
| 2017/0083682 A1* | 3/2017 | McNutt | A61N 5/1031 | |
| 2017/0140551 A1* | 5/2017 | Bauer | G06K 9/6256 | |
| 2018/0055407 A1* | 3/2018 | Wager | A61B 5/4076 | |
| 2019/0051398 A1* | 2/2019 | Zankowski | G06K 9/6288 | |
| 2019/0159737 A1* | 5/2019 | Buckler | G16H 30/40 | |
| 2019/0172197 A1* | 6/2019 | Buckler | G06T 5/003 | |
| 2019/0180438 A1* | 6/2019 | Buckler | G06T 7/0014 | |
| 2019/0192285 A1* | 6/2019 | Wong | A61B 5/4851 | |
| 2019/0244348 A1* | 8/2019 | Buckler | G06T 5/003 | |
| 2019/0371450 A1* | 12/2019 | Lou | G16H 50/30 | |
| 2020/0011950 A1* | 1/2020 | Tiwari | G01R 33/5608 | |
| 2020/0105413 A1* | 4/2020 | Vladimirova | G16H 15/00 | |
| 2020/0126207 A1* | 4/2020 | Saltz | G06T 7/0012 | |
| 2020/0138360 A1* | 5/2020 | Fan | A61B 5/441 | |
| 2020/0202516 A1* | 6/2020 | Kao | G06N 3/0481 | |
| 2021/0217167 A1* | 7/2021 | Lee | G06N 3/0454 | |
| 2021/0228079 A1* | 7/2021 | Betrouni | G16H 50/20 | |
| 2021/0272701 A1* | 9/2021 | Jones | G16H 10/60 | |

* cited by examiner

SYSTEM AND METHOD FOR OUTCOME-SPECIFIC IMAGE ENHANCEMENT

CROSS-REFERENCE TO RELATED APPLICATIONS

This application claims the benefit of U.S. Patent Application No. 62/813,950, filed Mar. 5, 2019, which is hereby incorporated by reference in its entirety.

FIELD OF THE INVENTION

The present invention is directed in general to a system and method for outcome-specific image enhancement; and more particularly to a quantitative method for detecting an outcome or disease specific signal from medical image data, using a machine learning algorithm to extract the best signal model of the disease specific signal, and using the best signal model on subject-specific image data to display the severity of the disease specific signal for that subject.

BACKGROUND OF THE INVENTION

Medical imaging refers generally to any number of techniques used to visualize the interior of a patient's body. There are many different types of imaging devices, each using a unique modality to produce a different type of resultant image which provides a different type of information. These devices and modalities are generally referred to as radiology. Examples include x-ray radiography, magnetic resonance imaging or MRI, ultrasound, computer tomography or CT and nuclear imaging such as positron emission tomography or PET. Selection of which modality or modalities is used for a patient depends on the desired information sought by the treating physician. For instance, x-ray and CT may be used to interrogate dense tissues, MRI can interrogate soft tissue and PET can be used to image functional processes which can then be correlated with CT or MRI location data to identify the anatomical location of the imaged activity. By way of example, tumor growth activity may be imaged by PET with MRI imaging identifying the responsible tissue/organ.

Despite advances in machine technologies to create and improve medical imaging modalities and image results, review and interpretation of these medical imaging results continues to rely upon the experience and opinion of highly trained radiologists. While there have been some technologies which enhance/condition the images to aid the radiologist in developing an interpretation of the image, such interpretations continue to be subject to human bias and error. That is, a series of radiologists may each review the same images and come to differing conclusions. This subjectivity may lead to adverse patient results. Additionally, a radiologist may overlook, or not even be aware of, small deviations within a patient image when compared with a "typical" control image. Such deviations may be indicative of an underlying disease state or other clinical presentation which may not become apparent to a radiologist until follow up imaging is performed after the disease/condition has progressed and worsened.

Thus, there is a need for computer-based artificial intelligence system for objective image analysis and interpretation. This system may further detect and identify miniscule deviations which may be overlooked by the human eye, thereby leading to earlier detection and intervention. The present invention fills these needs as well as other needs.

SUMMARY OF THE INVENTION

In one aspect, the present invention is directed to a computer-implemented method programmed for execution in a computing environment for predicting an outcome specific signal (OSS) in a plurality of test subject digital images of a test subject. The plurality of test subject digital images includes test subject image data that represents a volumetric space containing anatomy of the test subject and a volumetric background that does not contain the volumetric space containing anatomy of the test subject. Utilizing a processor, the method includes the step of providing a plurality of first digital images including first image data representative of a plurality of outcome subjects with a pre-identified specific outcome. The first image data for each of the plurality of outcome subjects defines a volumetric space containing a target anatomy of the respective outcome subject and a volumetric background that does not contain the volumetric space containing anatomy of the respective outcome subject. The method further includes the step of providing a plurality of second digital images including second image data representative of a plurality of control subjects not having the pre-identified specific outcome. The second image data for each of the plurality of control subjects defines a volumetric space containing the target anatomy of the respective control subject and a volumetric background that does not contain the volumetric space containing anatomy of the respective control subject.

The method also includes the steps of detecting an outcome specific signal (OSS) located in the volumetric space defined by the first image data and the volumetric space defined by the second image data, and extracting the volumetric space containing the detected OSS from the volumetric background in the first image data and the second image data, wherein the volumetric space containing the detected OSS includes the target anatomy. The extracted volumetric space in each of the first image data and the second image data is then divided into a first set of sub-regions. A set of image features is then determined for each of the first set of sub-regions. A global feature set (GFS) is then calculated by averaging the set of image features for each of the first set of sub-regions. A machine learning algorithm is used to select a subset of discriminant GFS to determine a best signal model (BSM) that distinguishes the plurality of outcome subjects from the plurality of control subjects.

The volumetric space containing the target anatomy is then extracted from the volumetric background in the test subject image data, and the extracted volumetric space in the test subject image data is divided into a second set of sub-regions. The subset of discriminant GFS are determined at each of the second set of sub-regions, and used in the BSM to generate the predicted OSS for each of the second set of sub-regions. A non-transitory computer readable medium having thereon computer executable instructions for execution in a computing environment for executing the method recited above is also provided in another aspect.

In another aspect, a computing system for predicting an outcome specific signal (OSS) in a plurality of test subject digital images of a test subject is provided. The system comprises an image data database, a memory for storing computer readable instructions, and a processor. The image data database includes a plurality of first digital images including first image data representative of a plurality of outcome subjects with a pre-identified specific outcome, wherein the first image data for each of the plurality of outcome subjects defines a volumetric space containing a target anatomy of the respective outcome subject and a volumetric background that does not contain the volumetric space containing anatomy of the respective outcome subject. The image data database further includes a plurality of second digital images including second image data representative of a plurality of control subjects not having the pre-identified specific outcome, wherein the second image data for each of the plurality of control subjects defines a volumetric space containing the target anatomy of the respective control subject and a volumetric background that does not contain the volumetric space containing anatomy of the respective control subject.

The processor is configured for executing the computer readable instructions to perform the steps of: detecting an outcome specific signal (OSS) located in the volumetric space defined by the first image data and the volumetric space defined by the second image data; extracting the volumetric space containing the detected OSS from the volumetric background in the first image data and the second image data, wherein the volumetric space containing the detected OSS includes the target anatomy; dividing the extracted volumetric space in each of the first image data and the second image data into a first set of sub-regions; determining a set of image features for each of the first set of sub-regions; determining a global feature set (GFS) by averaging the set of image features for each of the first set of sub-regions; utilizing a machine learning algorithm to select a subset of discriminant GFS to determine a best signal model (BSM) that distinguishes the plurality of outcome subjects from the plurality of control subjects; extracting the volumetric space containing the target anatomy from the volumetric background in test subject image data; dividing the extracted volumetric space in the test subject image data into a second set of sub-regions; and determining the subset of discriminant GFS at each of the second set of sub-regions, and using the subset of discriminant GFS at each of the second set of sub-regions in the BSM to generate the predicted OSS for each of the second set of sub-regions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above-mentioned and other features and advantages of this invention, and the manner of attaining them, will become apparent and be better understood by reference to the following description of the invention in conjunction with the accompanying drawings, wherein.

DETAILED DESCRIPTION OF THE INVENTION

Generally, the tools and methods described herein for implementing the system for outcome-specific image enhancement and other features described herein may be through the use of hardware, software or a combination thereof.

This document is organized as follows. In the first section, a general overview of the method and techniques included in the present invention is described. In the next section, an exemplary system that may be used to implement the method is illustrated and described. Finally, an exemplary embodiment utilizing the method and system of the present invention is provided.

The present invention is generally directed to a method for outcome-specific image enhancement, and more particularly to a quantitative method for detecting an outcome or disease specific signal from medical image data, using a machine learning algorithm to extract the best signal model of the disease specific signal, and using the best signal model on subject-specific image data to display the severity of the disease specific signal for that subject. Although the following discussion and the present invention are described in relation to brain abnormalities, injury or disease, it should be understood that the invention is also applicable to other areas of human anatomy where biological imaging technology is used to identify and characterize abnormalities, injury or disease.

Figure 1:
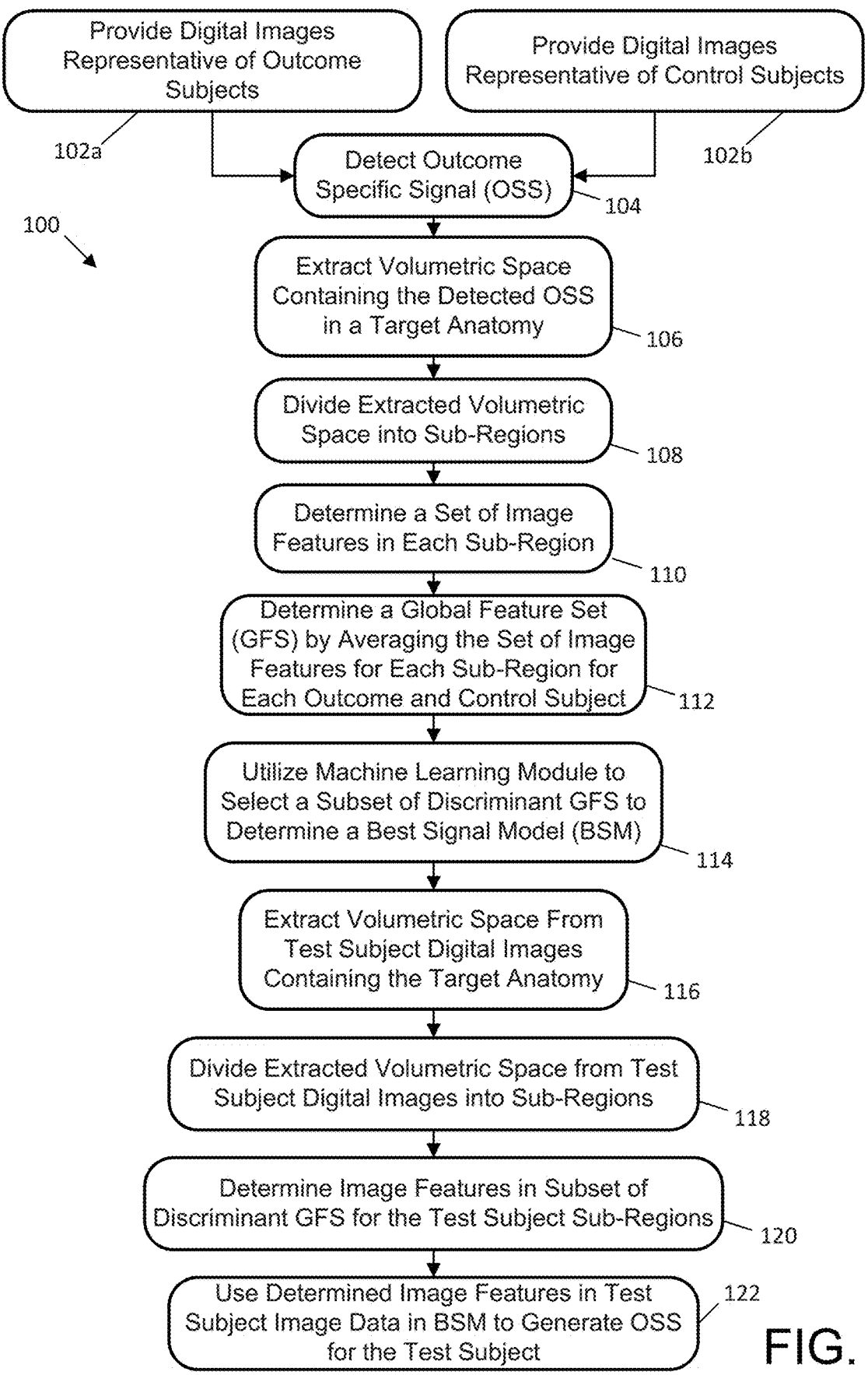
FIG. 1 is a flow chart illustrating an exemplary method for implementing one or more aspects of the present invention.

With reference to FIG. 1, a flow diagram is provided to illustrate one exemplary method 100 that is implemented in accordance with an aspect of the present invention. This aspect includes a computer-implemented method programmed for execution in a computing environment for predicting an outcome specific signal (OSS) in a plurality of test subject digital images of a test subject. The test subject may be, for example, a person (i.e., patient) that is seeking a prediction and/or subsequent diagnosis by a medical professional in regard to whether a certain abnormality, injury or disease is present in a target anatomy of the test subject. The plurality of test subject digital images includes test subject image data that represents a volumetric space containing a target anatomy of the test subject and a volumetric background that does not contain the volumetric space containing anatomy of the test subject.

At step 102*a*, method 100 provides a plurality of first digital images including first image data representative of a plurality of outcome subjects with a pre-identified specific outcome. An outcome subject is a person that has a known or previously diagnosed outcome (i.e., abnormality, injury or disease) in the target anatomy, wherein the severity or degree of the abnormality, injury or disease may also be known. The first image data for each of the plurality of outcome subjects defines a volumetric space containing the target anatomy of the respective outcome subject and a volumetric background that does not contain the volumetric space containing the target anatomy of the respective outcome subject.

At step 102b, the method provides a plurality of second digital images including second image data representative of a plurality of control subjects not having the pre-identified specific outcome. A control subject is a person that does not have the known or previously diagnosed outcome that is present in the target anatomy of the outcome subject. The second image data for each of the plurality of control subjects defines a volumetric space containing the target anatomy of the respective control subject and a volumetric background that does not contain the volumetric space containing anatomy of the respective control subject.

At step 104, the method includes detecting an outcome specific signal (OSS) located in the volumetric space defined by the first image data and the volumetric space defined by the second image data. At step 106, the method then includes extracting the volumetric space containing the detected OSS from the volumetric background in the first image data and the second image data, wherein the volumetric space containing the detected OSS includes the target anatomy. The extracted volumetric space in each of the first image data and the second image data is then divided into sub-regions at step 108. A comprehensive set of image features are then computed or otherwise identified for each sub-region at step 110. In general, the computation or identification of the image features includes transforming the first and second image data to produce both signal and texture information. In particular, for each sub-region in each first and second image data, image features are computed for signal (i.e., mean, standard deviation, skewness, kurtosis, and entropy) and for texture Gray-level co-occurrence matrix (GLCM) (i.e., angular second moment, correlation, contrast, dissimilarity, entropy, homogeneity, marginal entropy and mutual information). Thereafter, a global-feature-set (GFS) is then computed by averaging the set of image features for each sub-region (standard mean of the per-subregion features) at step 112. Further, a machine learning algorithm is used at step 114 to select a subset of discriminant GFS to determine a best signal model (BSM) (e.g. formula) that distinguishes the plurality of outcome subjects from the plurality of control subjects. The subset of discriminant GFS may be an image feature or variable that has the ability to distinguish between the control subject and the outcome subject. For example, the machine learning algorithm "trains" itself by selecting a set of image features that separate the first image data from the second image data on a subset of the first and second image data, and "tests" the performance of the image features on the remainder of the first and second image data. This process is repeated many times, and the image features that are the highest performing (e.g., selected the most times) comprise the subset of discriminant GFS. While many variables/features have some ability to separate cases from controls (they have some predictive power), only the best (e.g., ten or fewer) are used to construct the BSM. The additional features, while exhibiting differences between the outcome and control subjects, do not add much practical benefit to the BSM. For example, the present method may use the BSWiMS method to select a subset of discriminant GFS.

At step 116, the method further includes extracting the volumetric space containing the target anatomy from the volumetric background in the test subject image data, and followed by dividing the extracted volumetric space in the test subject image data into sub-regions at step 118. The image features in the subset of discriminant GFS are computed or otherwise identified at each of the sub-regions of the test subject image data at step 120, and then used in the BSM to generate the predicted OSS for each of the sub-regions of the test subject image at step 122.

Figure 2:
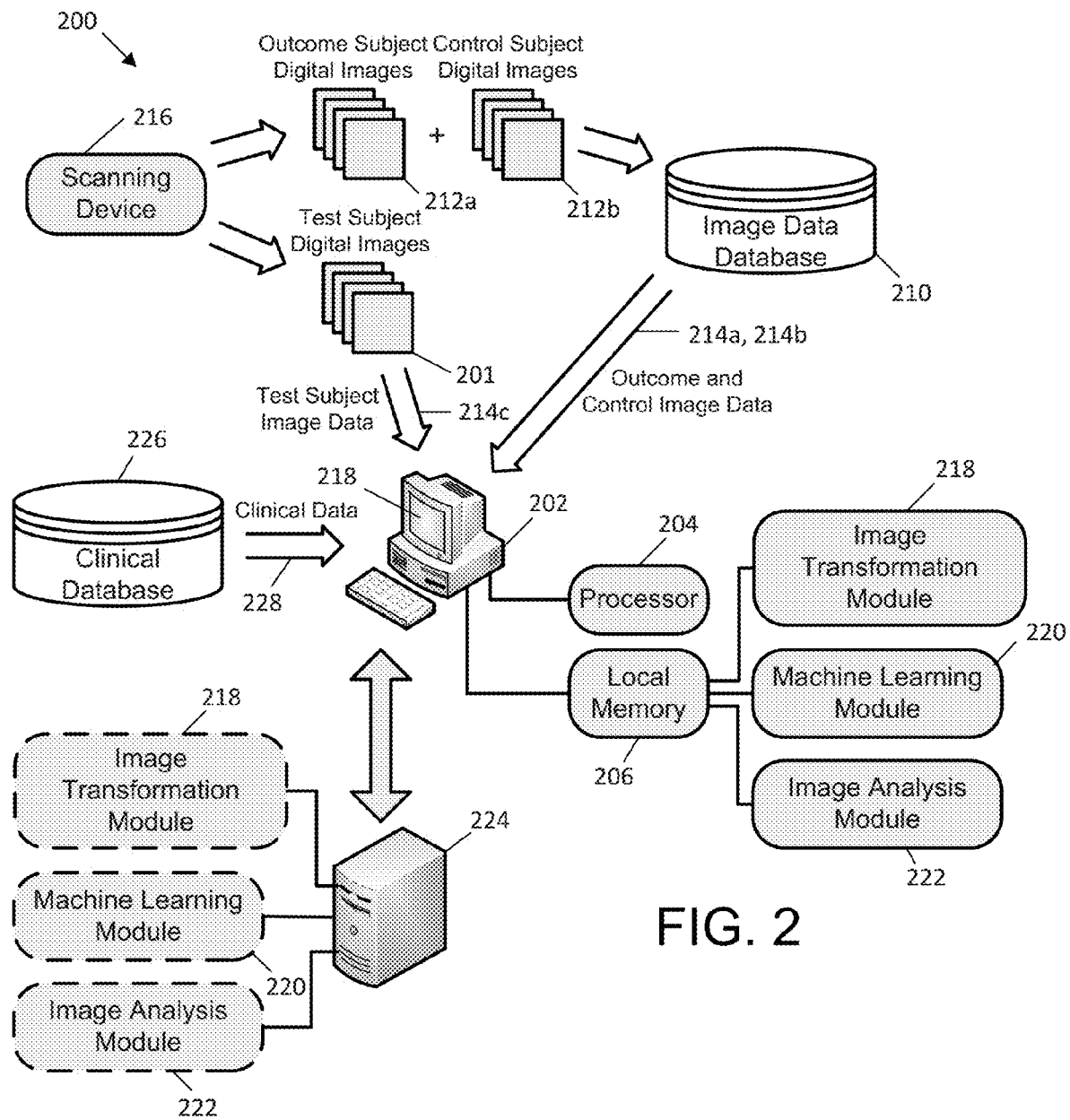
FIG. 2 is a schematic drawing of a system that may be used to implement the present invention set forth in FIG. 1.
Figure 3:
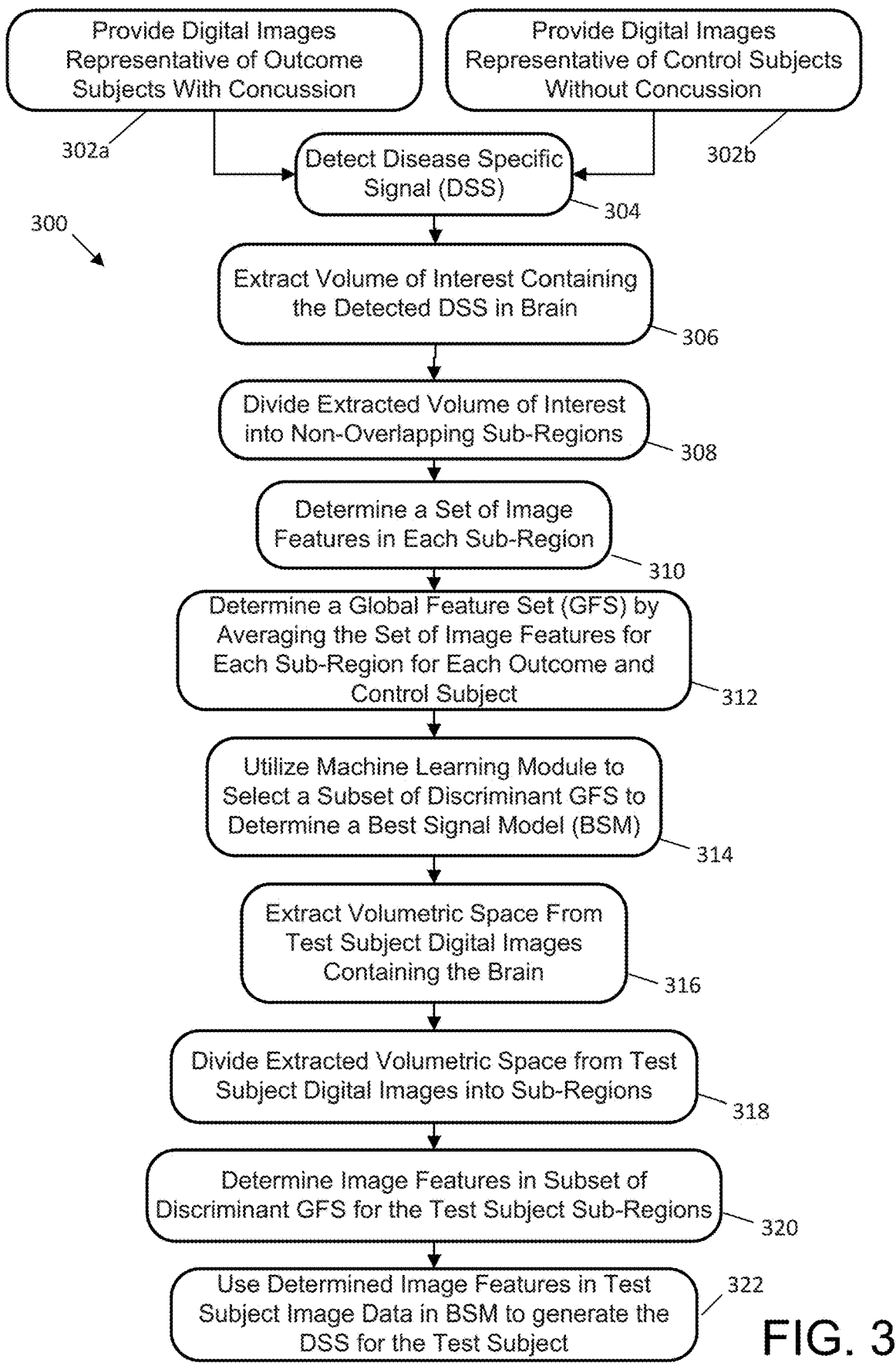
FIG. 3 is a flow chart illustrating another exemplary method for implementing one or more aspects of the present invention.

Having described an exemplary method 100 including certain aspects of the present invention, a system will now be described that may be used to implement method 100. In particular, FIG. 2 illustrates a system 200 that may be used to predict an OSS in a plurality of test subject digital images 201 of a test subject related to the target anatomy. System 200 may include a computing device 202 including a processor 204, a memory 206, and a display 208 that is configured for executing computer readable instructions to implement the functionality described herein. Computing device 200 may be any type of computing device including, but not limited to, a desktop computer, laptop computer, mobile device, and the like. System 200 may further include an image data database 210 that is configured for storing a plurality of digital images 212a including image data 214a representative of the target anatomy of one or more outcome subjects that have been diagnosed with a disease, injury or abnormality. Image database 210 is also configured for storing a plurality of digital images 212b including image data 214b representative of the target anatomy of one or more control subjects that have no history of the disease, injury or abnormality diagnosed in the outcome subjects. It should also be understood that the plurality of test subject digital images 201 along with the related test subject image data 214c may also be stored in image database 210, or communicated directly to computing device 202 after being created for further processing in accordance with the aspects of the present invention, which will be discussed in more detail below.

Digital images 201, 212a, 212b may be generated using a scanning device 216, such as, but not limited to, a magnetic resonance imaging (MRI) scanner, computerized tomography (CT) scanner, X-ray, mammography device, digital pathology device, positron emission tomography (PET) scanner, or similar device, that is capable of generating the image data 214a, 214b, 214c. Image data may be any type of digital data that represents images or pictures of the body. The image data 214a, 214b, 214c may further define a volumetric space containing the target anatomy of the respective subject and a volumetric background that does not contain the volumetric space containing anatomy of the respective subject. Processor 204 may operate to display any of the image data 214a, 214b, 214c on display 208. The local memory 206 of computing device 202 may include computer readable instructions that are representative of an image transformation module 218, a machine learning module 220 and an image analysis module 222, each of which will be described with reference to the exemplary embodiment provided below. While FIG. 2 shows the modules 218, 220 and 222 being stored in local memory 206 of computing device 202, it should be understood that these modules 218, 220 and/or 222 may be additionally or alternatively be stored in a remote memory 224, such as a server, that is accessible to computing device 202.

System 200 may further include a clinical database 226 that is configured for storing clinical data 228 that may be communicated to computing device 202. Clinical data may be any non-image data that is specific to a particular subject, such as, but not limited to, standard demographic data (gender, age, sex, height, weight), clinical history data (cholesterol test values, responses to clinical questionnaires), previous conditions (diagnosis of a particular disease, concussions, illness), family history (hypertension, diabetes), current diagnosis (concussion severity, symptoms, location of injury, injury name), or any other information in a patient history file. Clinical data may be used by machine learning module 220 to associate or correlate one or more image features, and perhaps the sub-set of discriminant GFS, to an outcome (e.g., concussion, etc.) of an outcome subject, a degree of the outcome (e.g., grade of concussion), and/or time of recovery (e.g., 4 weeks to recover).

As provided above, the various components of the system 200 are configured to communicate or otherwise exchange information and/or data to each other. In order to facilitate this communication, it should be understood that the components may operate in a networked environment. The network may be any type of network, such as a wide area network (WAN) or local area network (LAN) through a wired or wireless connections.

Having described the methodology of the present invention and a system for implementing the same, an exemplary embodiment of the method will now be described with reference to a situation where it is desired to predict the presence and/or severity of a traumatic brain injury (mTBI) or concussion (hereinafter collectively referred to as a "concussion") in a test subject. With reference to FIGS. 2-9, a method 300 may provide a plurality of first digital images 212a including first image data representative of a plurality of outcome subjects with a known concussion at step 302a. At step 302b, method 300 provides a plurality of second digital images 212b including second image data representative of a plurality of control subjects that have no medical history of a concussion. The first and second image data may be a collection of MRI image data generated from scanning device 216 containing MPRAGE and Diffusion-Tensor (DTI) images with Apparent Diffusion Coefficient (ADC) and Fractional Anisotropy (FA) images. The first and second image data may be stored in image data database 210. The first and second image data may then be communicated to computing device 202.

MRI images are "tuned" to be sensitive to various types of tissue, pathology, etc. For example, MRI acquisition pulse sequences are configured to be more or less sensitive to fat or water content, generating pictures that have brighter and darker regions according to which signals (fat/water) the sequence is sensitive to. Other types of images (CT/X-ray/ Mammography) generate pictures where the highest density generates the brightest signal. PET signals are based on where the radioactive tracer originates from and how much tracer is released. In general, this system and method combines information from multiple images 212a, 212b from a plurality of outcome and control subjects to detect an outcome specific signal (OSS), such as a disease specific signal (DSS), at step 304 that is too subtle to be revealed in a set of MRI images from a single subject. In order to detect the DSS, the image transformation module 218 in computing device 202 includes computer executable instructions that are configured for transforming the first and second image data. For example, the first and second image data are processed by image transformation module 218 to generate derivative images, such as fractals (e.g., fractal dimension), wavelets and anatomic segmentations, and also processed by the Gray-level Co-occurrence matrix, to convert the patterns and textures of the first and second image data into a set of numbers so they can be processed by the machine learning algorithms. The transformed first and second image data is then communicated to machine learning module 220, which partitions the first and second image data into a training set and a testing set. The training set is then processed to select the features/variables (e.g., numerically transformed patterns and/or textures) that seem to best separate or identify the outcome. The selected features/variables are then tested on the testing set to assess how well those features/variables do at separating the outcome set forth in the clinical data. The steps of partitioning and processing of the training and testing sets is then repeated many times. The features/ variables that have the highest frequency of being selected, or the best performance of separating the outcome, constitute the DSS. The DSS may then be stored in local memory 206 or server 224.

At step 306, the exemplary method then includes extracting the volumetric space containing the detected DSS from the volumetric background in the first image data and the second image data (i.e., volume of interest), wherein the volume of interest includes the target anatomy, in this instance, a human brain. In other words, the volume of interest is whatever portion of the image that contains the anatomy relevant to the outcome/disease. For example, the air/background in the image may be excluded from the volume of interest as it has no relevance to the target anatomy. In another example, if liver abnormalities are being analyzed, exclude all parts of the image that do not show liver tissue from the volume of interest. Moving back to the exemplary embodiment, the first and second image data may be segmented using a BRAIN atlas based on ICBM 152 Nonlinear atlases (2009) to separate the skull from brain tissue regions of interest. For example, the BRAIN atlas may include a series of sections along different planes of the brain (e.g., coronal, sagittal, and frontal planes) wherein each brain structure may be assigned coordinates to define the volume of the brain. In particular, the segmentation procedure may be atlas-based using a multi-resolution, step-wise approach using a normalized Mattes-Mutual information metric with SPLINE deformation. The atlas may be morphed into each subject image data set using a back-transformation.

Figure 4:
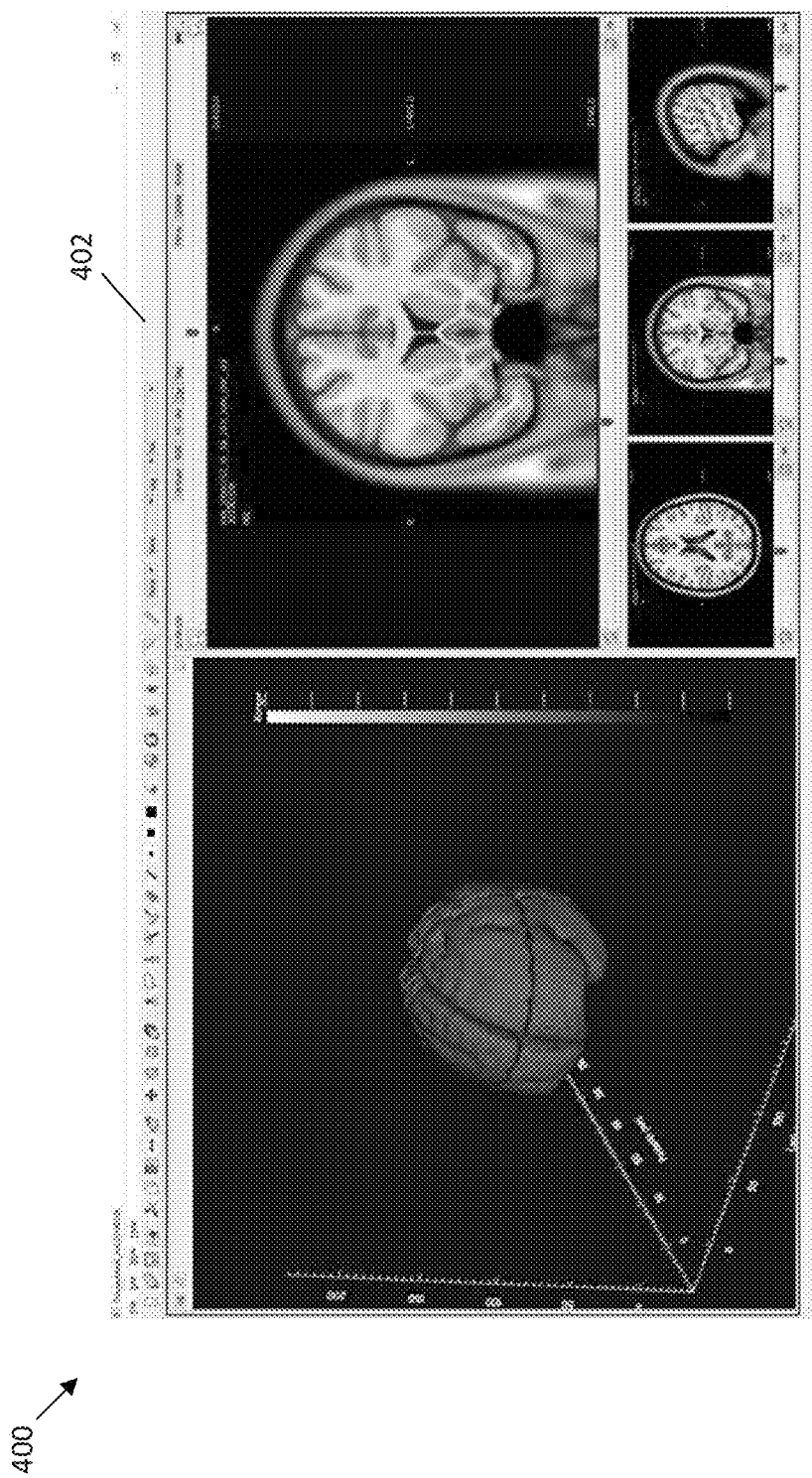
FIG. 4 is an exemplary user interface displaying MRI images and a volume of interest divided in sub-regions.

The extracted volume of interest (i.e., brain) in each of the first image data and the second image data may then be divided into non-overlapping sub-regions at step 308. FIG. 4 illustrates an example of the volume of interest 400 (i.e., brain) from first or second image data including the sub-regions 400a, 400b, 400c, 400d (e.g., eight sub-regions but only four shown) is shown on a user interface 402 of display 208. Tools and features may be utilized through user interface 400 to view, analyze and/or manipulate the volume of interest 400 using computing device 202.

Figure 5:
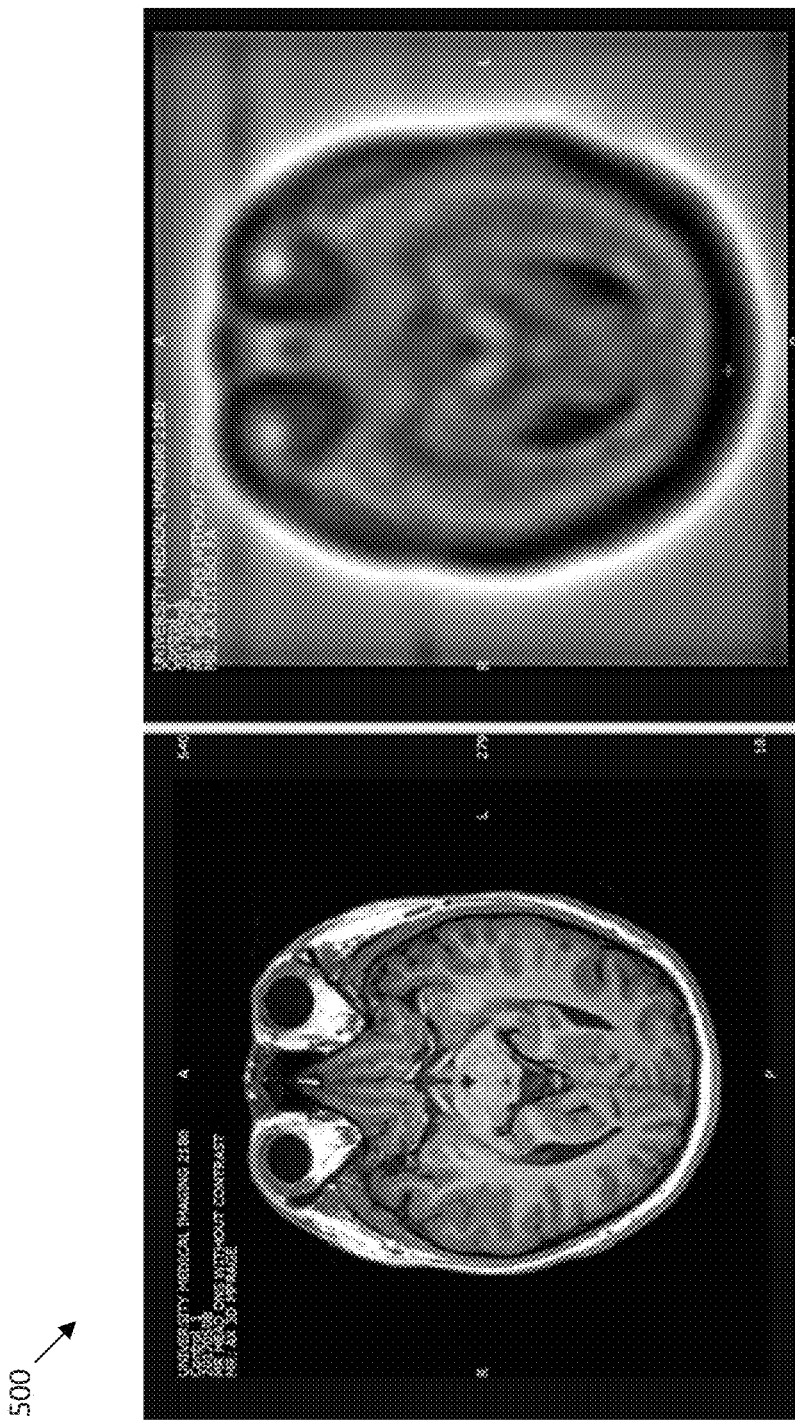
FIG. 5 is an MRI image including a local fractal dimension.
Figure 6:
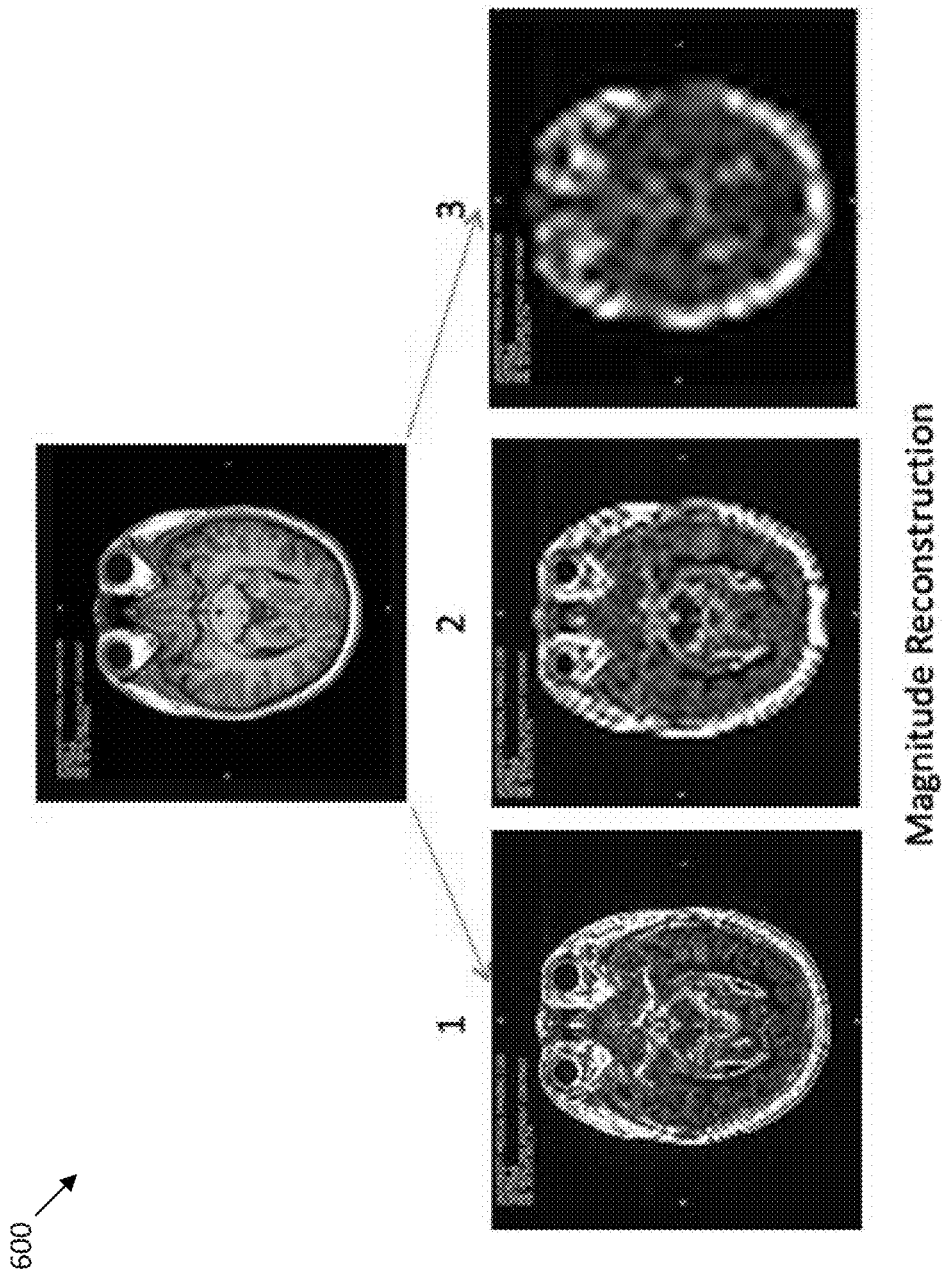
FIG. 6 is a MRI image showing 3 levels wavelet.

Method 300 then operates to determine or otherwise identify a comprehensive set of image features for each sub-region 400a, 400b, 400c, 400d in each of the first and second image data 214a, 214b using image analysis module 222 at step 310. For the example related to post-concussive brain abnormalities discussed herein, the computation or identification of the image features to produce both signal (i.e., mean, standard deviation, skewness, kurtosis, and entropy) and texture (i.e., angular second moment, correlation, contrast, dissimilarity, entropy, homogeneity, marginal entropy and mutual information) information may that include, for example, the local fractal dimension 500 as seen in FIG. 5, and the 3 levels of wavelet decomposition 600 as seen in FIG. 6. The 3 levels of wavelet decomposition uses magnitudes of High-Low (HL), Low-High (LH) and High-High (HH) sub-bands at each level, which is derived information about the image signal behavior that may be more sensitive to detecting the outcome/disease. The Gray-level co-occurrence matrix data may also be used to produce signal and/or texture information for each sub-region 400a, 400b, 400c, 400d.

At step 312, the image analysis module 22 operates to extract all of the image features determined at step 310 for each sub-region 400a, 400b, 400c, 400d for each subject, and compute the average of the sub-regions 400a, 400b, 400c, 400d to generate a global feature set (GFS) for each outcome subject and control subject. Further, if certain clinical data were significant in constituting the BSM, they would be incorporated in step 312, where they would added to the image-derived variables to make the GFS.

At step 314, machine learning module 220 uses a machine learning algorithm to select a subset of discriminant GFS to determine a best signal model (BSM). In particular, the GFS for each of the outcome subjects and each control subject is extracted and placed in a labeled data set. All of the GFS data is conditioned by adjusting for age, height, sex, and weight differences, and then further control-conditioned (to normalize to the distribution of the control image data) and Z-transformed, to ensure that all variable differences have a similar relative magnitude and to prevent some values from having a disproportionate effect. The GFS data is conditioned by normalizing it to standardize it across human physiology (e.g., aging, size) and/or signal variations from data set to data set (e.g., balancing the histogram to standardize the range of brightness to darkness). The machine learning module 220 includes computer executable instructions that are applied to the GFS to extract the BSM separating the outcome subjects from the control subjects. For example, the BSM (p) can be extracted by extracting the best features $(x\downarrow i)$ and learn the coefficients $(\beta\downarrow i)$ of the logistical model:

$$p = \frac{b\uparrow\beta\downarrow 0 + \beta\downarrow 1 \times \downarrow 1 + \beta\downarrow 2 \times \downarrow 2}{b\uparrow\beta\downarrow 0 + \beta\downarrow 1 \times \downarrow 1 + \beta\downarrow 2 \times \downarrow 2 + 1} =$$

$$\frac{1}{1 + b\uparrow -(\beta\downarrow 0 + \beta\downarrow 1 \times \downarrow 1 + \beta\downarrow 2 \times \downarrow 2)}$$

In the above logistical model, b represents the calibration constant. The above-referenced logistical model may be a bagged average of 100 repetitions, for example, of stagewise-model-selection (BSWiMS). BSWiMS is a machine-learning process that repetitively selects variables that have a significant association with the outcome, then compares the frequency of the variables found in each repetition to generate the final selection.

Figure 7:
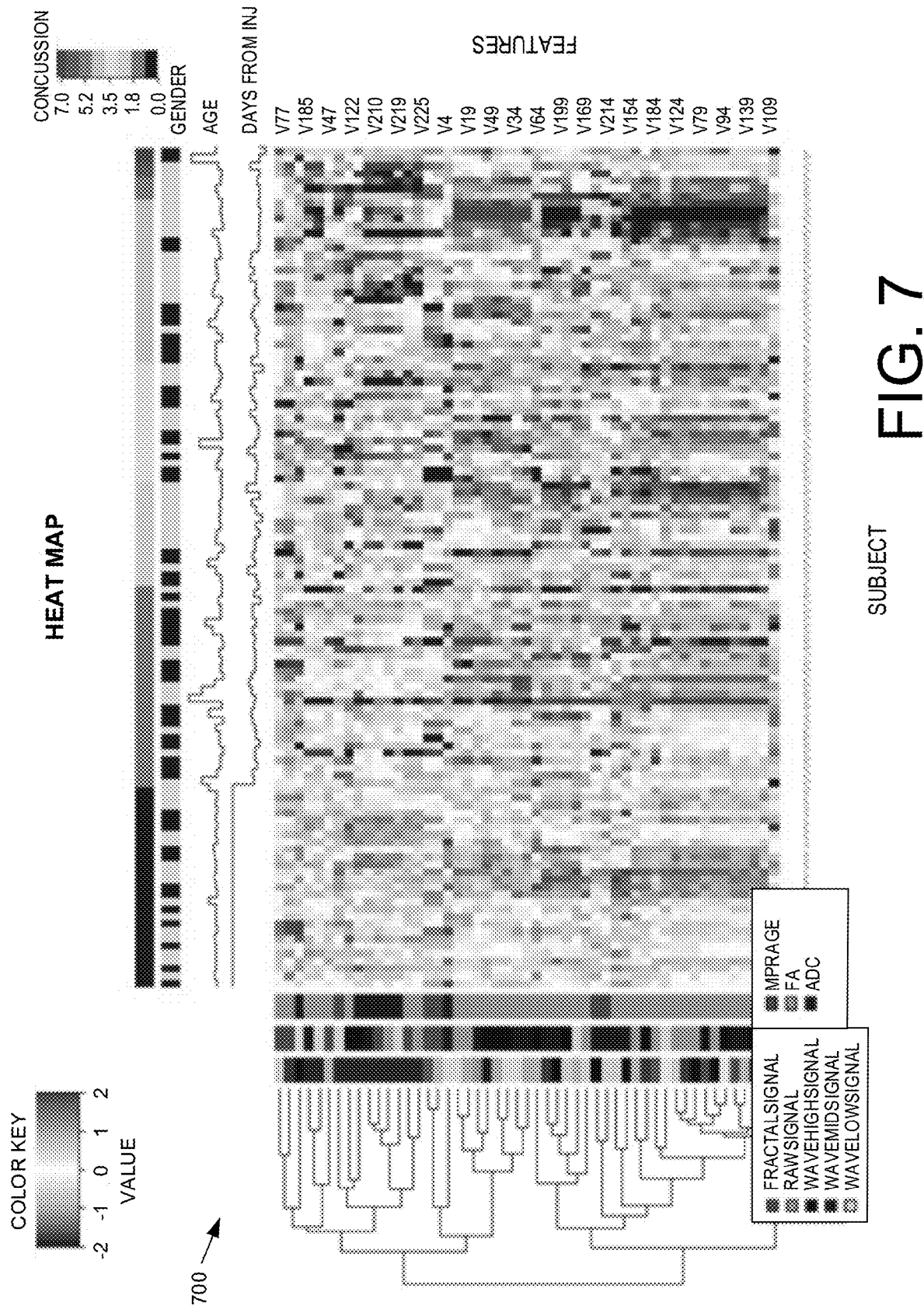
FIG. 7 is a heat map including a best signal model obtained by one aspect of the present invention.

As best seen in FIG. 7, the results of steps 304-314 provides a display of a heat map 700 that comprises the BSM and thereby enhances the location of the subtle brain abnormalities. The color key in FIG. 7 is the value (e.g., −2 to +2) of a particular feature/variable as measured for a particular subject. The top color bar shows how many concussions each subject has had (including the test subject). Below the top color bar, there is another color bar that shows subject gender (pink/blue) and below that, the two graphs indicate the age of the subject (higher=older) and the time from injury (note that the flat line was arbitrarily set at a large value, since these subjects were control subject and did not have any injury). Together, they give information about the subjects that can be visually compared to the color values of individual variable measurement values below. The left y-axis shows information about the origin of the variables (e.g., which MRI series the variable was derived from, and what type of variable—e.g. raw signal or derivative transform, like fractals or wavelets). The right y-axis shows the individual variables being displayed in the heat map and the lower x-axis shows the individual subjects. While this map may not derive the predictive DSS, it can visually help the viewer see that there are differences between each outcome group. If the map colors were uniformly distributed, it would suggest there was no particular variables which behave differently for different groups.

The BSM obtained in step 314 is used to predict a DSS on the plurality of test digital images 201 of a test subject. For example, MRI images from a test subject containing MPRAGE and DTI with ADC and FA series may be used. Once the BSM is found using machine learning module 220, the BSM is computed in a similar manner for the test subject data 214c and the resulting BSM value is predictive of the outcome. In a non-limiting and generic example, a population of people who wear red or blue hats is analyzed to see if they vote D or R. Analysis finds that people wearing red hats are quite likely to vote R. Given this model, when a new person arrives at the polls wearing a red hat, the system predicts they will vote R.

Figure 8:
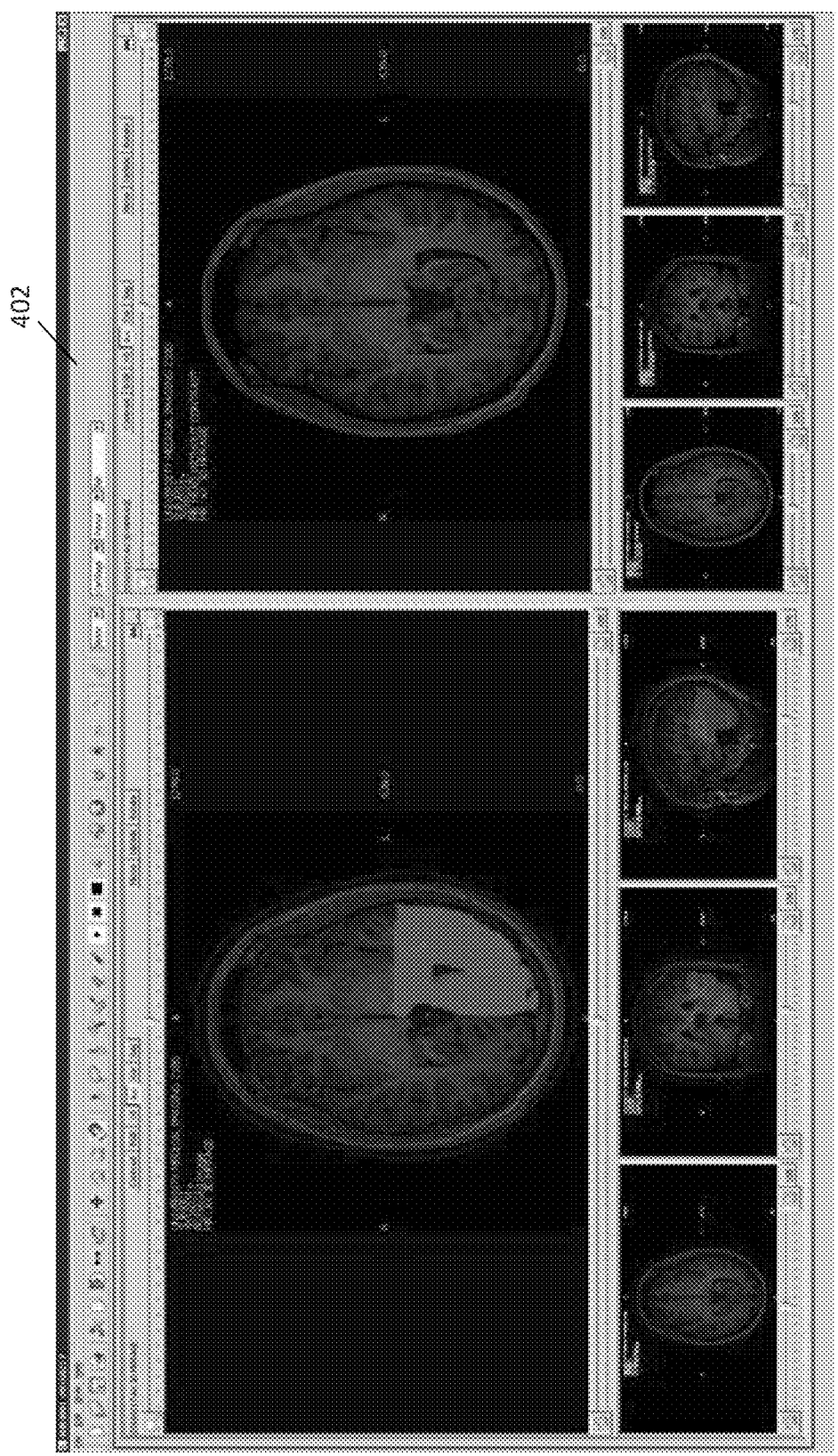
FIG. 8 is an exemplary user interface showing an extracted volumetric space containing the target anatomy of a test subject.

As best seen in FIG. 8, method 300 further includes extracting the volumetric space containing the target anatomy (i.e., brain) from the volumetric background in the test subject image data (e.g., MRI image data) using image analysis module 222 at step 316, dividing the extracted volumetric space in the test subject image data into sub-regions at step 318 using the Altlas-based method provided in step 306. This information may then be optionally displayed on user interface 402 of display 208.

At step 320, the specific image features in the subset of discriminant GFS are then computed or otherwise identified at each sub-region for the test subject image data using image transformation module 218. For example, each MRI image may be transformed using the Local Fractal Dimension, the 3 Level Wavelet decomposition with magnitudes of HL, LH and HH at every level, plus the grey-level co-occurrence matrix data. For each sub-region on every image/transform, the signal and texture may be computed. The signal values are whatever value is assigned to each pixel/voxel in the image data, and the texture is computed by the GLCM formulas, which represent texture/patterns. The signal may include, but is not limited to, the mean, standard deviation, skewness, kurtosis and entropy. Further, the texture GLCM may include, but is not limited to, angular second moment/ASM, correlation, contrast, dissimilarity, entropy, homogeneity, marginal entropy and mutual information.

The image features in the subset of discriminant GFS computed or otherwise identified in step 320 are then used in the BSM to generate the DSS at each sub-region of the test subject image data at step 322 to predict the presence, location, and/or severity of a concussion in the test subject. In particular, the signal features of the test subject image data is conditioned to the control subject image data by adjusting for sex, age, height and weight, and then Z-transformed, similar to the conditioning that takes place in step 314. A DSS (i.e., outcome enhanced signal) then predicted at each sub-region of test subject image data using machine learning module 220 by combining the logistic-learned coefficient and the GFS required predicting the outcome using the following model:

$$s(x,y,z) = \beta\downarrow 0 + \beta\downarrow 1 \times \downarrow 1 + \ldots + \beta\downarrow q \times \downarrow q$$

where $s(x,y,z)$ is the predicted DSS, $\beta\downarrow i$ is the logistic learned coefficient, and are the best features/variables required to separate or identify the outcome. The logistic learned coefficient is provided by machine learning module 220 which provides the formula (e.g., coefficients, x variables to generate the DSS).

Figure 9:
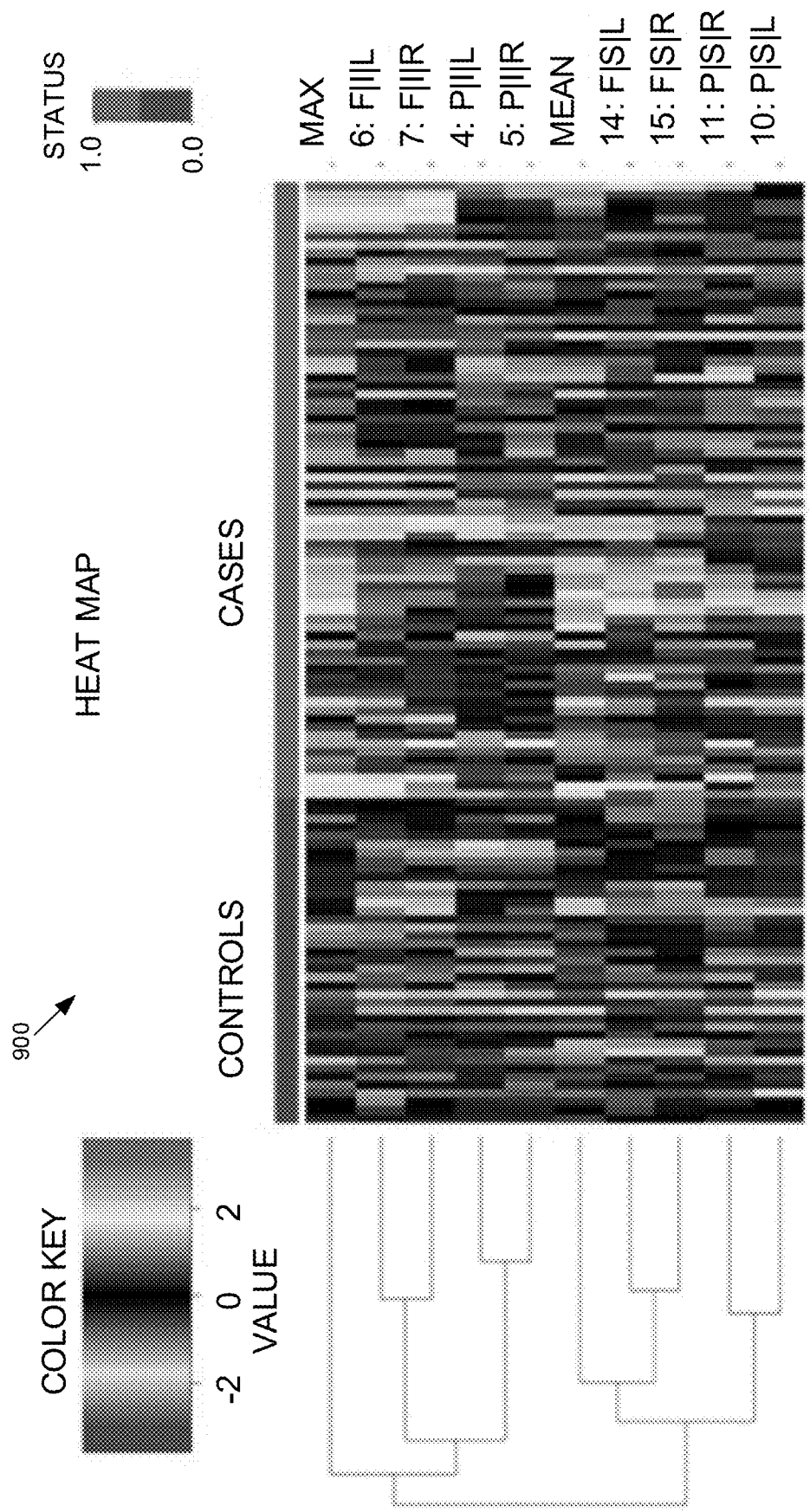
FIG. 9 is a heat map illustrating the BSM predictive values for each sub-region of a test subject.

As a result of the aforementioned analysis, and as best seen in FIG. 9, image analysis module 222 may be used to display a heat map 900 on user interface 402 of display 208 to illustrate BSM predictive values for each sub-region of the test subject image data for the test subject. Heat map 900 shows the color-coded value of the key variables by subject/sub-region. The subjects are grouped into cases and controls, so that differences in variable values between groups can be seen visually. Cases are subjects who exhibit the outcome, while controls are similar subjects who do not exhibit the outcome (or disease). The labeling in FIG. 9 (e.g., Max, 6:F|I|L, 7: F|I|R, etc.) identify anatomical sub-regions (e.g. F|I|L=Frontal Inferior Left), plus a global maximum and global average. The color coding in this example shows that the signals are not uniform across sub-regions, suggesting that the DSS is able to pick up sub-regional disease/injury. In other words, FIG. 9 is a visual test/indicator that differences exist between the cases/controls, suggesting that a reliable DSS can be generated from this data set. The brackets shown on the left side of heat map 900 show associations between some variables, for example, the min, max, mean and standard deviation of raw MRI signal are all based on the raw MRI signal. These brackets may also show associations between other variables, for example, height and weight. While the heat map may not generate the DSS, it may be used to predict the DSS. For example, if the colors appear to be different for different groups/classes of subjects, then this suggests that there are variables which will be able to predict the DSS. In FIG. 9, the right y-axis shows that each row represents a different anatomical region of the brain, plus the maximum global and mean global signal of the DSS. Visually, it can be seen in this example that some rows are much more yellow and some are more blue, suggesting that the DSS is significantly different for different anatomical regions, or that the DSS is able to predict concussive injury location on a regional level, not just that a subject is likely to have concussive injury.

In another aspect, it should be understood that the methods set forth above may be embodied in computer readable instructions stored on a non-transitory computer readable medium.

It can be seen that the above-referenced exemplary systems and methods address the drawbacks and deficiencies that currently exist in this technological field. In particular, the present invention provides a novel, standardized, quantitative method for detecting a disease specific signal from medical image data using machine learning to extract the best signal model of the disease specific signal and using the best signal model on test subject image data to display the severity of the disease specific signal for that test subject. Another significant benefit is that the system and method operates to display on a reference image set (such as one that displays underlying anatomy) the collective abnormality derived from multiple image sets, and from information in three-dimensions. Typically, human experts review image data in 2D and are not able to simultaneously see/consider multiple image data sets or discern subtle differences in signal intensity or pattern.

From the foregoing, it will be seen that this invention is one well adapted to attain all the ends and objects hereinabove set forth together with other advantages which are obvious and which are inherent to the method and apparatus. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. As used herein, the terms "having" and/or "including" and other terms of inclusion are terms indicative of inclusion rather than requirement.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A computer-implemented method programmed for execution in a computing environment for predicting an outcome specific signal (OSS) in a plurality of test subject digital images of a test subject, wherein the plurality of test subject digital images includes test subject image data that represents a volumetric space containing anatomy of the test subject and a volumetric background that does not contain the volumetric space containing anatomy of the test subject, utilizing a processor the method comprising the steps of:

providing a plurality of first digital images including first image data representative of a plurality of outcome subjects with a pre-identified specific outcome, wherein the first image data for each of the plurality of outcome subjects defines a volumetric space containing a target anatomy of the respective outcome subject and a volumetric background that does not contain the volumetric space containing anatomy of the respective outcome subject;

providing a plurality of second digital images including second image data representative of a plurality of control subjects not having the pre-identified specific outcome, wherein the second image data for each of the plurality of control subjects defines a volumetric space containing the target anatomy of the respective control subject and a volumetric background that does not contain the volumetric space containing anatomy of the respective control subject;

detecting an outcome specific signal (OSS) located in the volumetric space defined by the first image data and the volumetric space defined by the second image data;

extracting the volumetric space containing the detected OSS from the volumetric background in the first image data and the second image data, wherein the volumetric space containing the detected OSS includes the target anatomy;

dividing the extracted volumetric space in each of the first image data and the second image data into a first set of sub-regions;

determining a set of image features for each of the first set of sub-regions;

determining a global feature set (GFS) by averaging the set of image features for each of the first set of sub-regions;

utilizing a machine learning algorithm to select a subset of discriminant GFS to determine a best signal model (BSM) that distinguishes the plurality of outcome subjects from the plurality of control subjects;

extracting the volumetric space containing the target anatomy from the volumetric background in the test subject image data;

dividing the extracted volumetric space in the test subject image data into a second set of sub-regions; and determining the subset of discriminant GFS at each of the second set of sub-regions, and using the subset of discriminant GFS at each of the second set of sub-regions in the BSM to generate the predicted OSS for each of the second set of sub-regions.

2. A method in accordance with claim 1, wherein the pre-identified specific outcome is a pre-identified specific disease.

3. A method in accordance with claim 2, wherein the outcome specific signal (OSS) is a disease specific signal (DSS).

4. A method in accordance with claim 1, wherein the outcome subjects and the control subjects are similar in at least one of sex, age, height, and weight.

5. A method in accordance with claim 1, wherein the target anatomy is a brain.

6. A method in accordance with claim 1, wherein the GFS is conditioned by adjusting for at least one of age, height, sex, and weight differences.

7. A non-transitory computer readable medium having thereon computer executable instructions for execution in a computing environment for predicting an outcome specific signal (OSS) in a plurality of test subject digital images of a test subject, wherein the plurality of test subject digital images includes test subject image data that represents a volumetric space containing anatomy of the test subject and a volumetric background that does not contain the volumetric space containing anatomy of the test subject, utilizing a processor the method comprising the steps of:

providing a plurality of first digital images including first image data representative of a plurality of outcome subjects with a pre-identified specific outcome, wherein the first image data for each of the plurality of outcome subjects defines a volumetric space containing a target anatomy of the respective outcome subject and a volumetric background that does not contain the volumetric space containing anatomy of the respective outcome subject;

providing a plurality of second digital images including second image data representative of a plurality of control subjects not having the pre-identified specific outcome, wherein the second image data for each of the plurality of control subjects defines a volumetric space containing the target anatomy of the respective control subject and a volumetric background that does not contain the volumetric space containing anatomy of the respective control subject;

detecting an outcome specific signal (OSS) located in the volumetric space defined by the first image data and the volumetric space defined by the second image data;

extracting the volumetric space containing the detected OSS from the volumetric background in the first image data and the second image data, wherein the volumetric space containing the detected OSS includes the target anatomy;

dividing the extracted volumetric space in each of the first image data and the second image data into a first set of sub-regions;

determining a set of image features for each of the first set of sub-regions;

determining a global feature set (GFS) by averaging the set of image features for each of the first set of sub-regions;

utilizing a machine learning algorithm to select a subset of discriminant GFS to determine a best signal model (BSM) that distinguishes the plurality of outcome subjects from the plurality of control subjects;

extracting the volumetric space containing the target anatomy from the volumetric background in the test subject image data;

dividing the extracted volumetric space in the test subject image data into a second set of sub-regions; and determining the subset of discriminant GFS at each of the second set of sub-regions, and using the subset of discriminant GFS at each of the second set of sub-regions in the BSM to generate the predicted OSS for each of the second set of sub-regions.

8. A method in accordance with claim 7, wherein the pre-identified specific outcome is a pre-identified specific disease.

9. A method in accordance with claim 8, wherein the outcome specific signal (OSS) is a disease specific signal (DSS).

10. A method in accordance with claim 7, wherein the outcome subjects and the control subjects are similar in at least one of sex, age, height, and weight.

11. A method in accordance with claim 7, wherein the target anatomy is a brain.

12. A method in accordance with claim 7, wherein the GFS is conditioned by adjusting for at least one of age, height, sex, and weight differences.

13. A computing system for predicting an outcome specific signal (OSS) in a plurality of test subject digital images of a test subject, the system comprising:

a) an image data database including:

i) a plurality of first digital images including first image data representative of a plurality of outcome subjects with a pre-identified specific outcome, wherein the first image data for each of the plurality of outcome subjects defines a volumetric space containing a target anatomy of the respective outcome subject and a volumetric background that does not contain the volumetric space containing anatomy of the respective outcome subject; and ii) a plurality of second digital images including second image data representative of a plurality of control subjects not having the pre-identified specific outcome, wherein the second image data for each of the plurality of control subjects defines a volumetric space containing the target anatomy of the respective control subject and a volumetric background that does not contain the volumetric space containing anatomy of the respective control subject;

b) a memory for storing computer readable instructions; and c) a processor configured for executing the computer readable instructions to perform the steps of:

detecting an outcome specific signal (OSS) located in the volumetric space defined by the first image data and the volumetric space defined by the second image data;

extracting the volumetric space containing the detected OSS from the volumetric background in the first image data and the second image data, wherein the volumetric space containing the detected OSS includes the target anatomy;

dividing the extracted volumetric space in each of the first image data and the second image data into a first set of sub-regions;

determining a set of image features for each of the first set of sub-regions;

determining a global feature set (GFS) by averaging the set of image features for each of the first set of sub-regions;

utilizing a machine learning algorithm to select a subset of discriminant GFS to determine a best signal model (BSM) that distinguishes the plurality of outcome subjects from the plurality of control subjects;

extracting the volumetric space containing the target anatomy from the volumetric background in test subject image data;

dividing the extracted volumetric space in the test subject image data into a second set of sub-regions; and determining the subset of discriminant GFS at each of the second set of sub-regions, and using the subset of discriminant GFS at each of the second set of sub-regions in the BSM to generate the predicted OSS for each of the second set of sub-regions.

14. A system in accordance with claim 13, wherein the pre-identified specific outcome is a pre-identified specific disease.

15. A system in accordance with claim 14, wherein the outcome specific signal (OSS) is a disease specific signal (DSS).

16. A system in accordance with claim 13, wherein the outcome subjects and the control subjects are similar in at least one of sex, age, height, and weight.

17. A system in accordance with claim 13, wherein the target anatomy is a brain.

18. A system in accordance with claim 13, wherein the GFS is conditioned by adjusting for at least one of age, height, sex, and weight differences.

* * * * *